United States Patent [19]

Kashihara et al.

[11] 4,228,124

[45] * Oct. 14, 1980

[54] FUMIGATING METHOD AND APPARATUS

[75] Inventors: Takanobu Kashihara; Fukuyasu Okuda; Masanaga Yamaguchi; Akira Nishimura, all of Ako, Japan

[73] Assignee: Earth Chemical Company, Ako, Japan

[*] Notice: The portion of the term of this patent subsequent to Jul. 31, 1996, has been disclaimed.

[21] Appl. No.: 42,424

[22] Filed: May 25, 1979

Related U.S. Application Data

[63] Continuation-in-part of Ser. No. 882,816, Mar. 2, 1978, Pat. No. 4,171,340.

[30] Foreign Application Priority Data

Feb. 27, 1979 [JP] Japan .................................. 54-23237

[51] Int. Cl.³ .......................... A61L 2/20; A01M 13/00
[52] U.S. Cl. ......................................... 422/36; 43/125;
43/129; 71/DIG. 1; 252/350; 422/1; 422/28; 422/37; 422/305; 424/40
[58] Field of Search ................. 422/1, 28, 36, 37, 305; 424/40; 43/125, 129; 71/DIG. 1; 252/350

[56] References Cited

U.S. PATENT DOCUMENTS

| | | | |
|---|---|---|---|
| 586,759 | 7/1897 | Cock | 422/305 |
| 1,652,291 | 12/1927 | Tanner | 422/305 |
| 2,047,973 | 7/1936 | Lawton et al. | 422/305 |
| 2,071,171 | 2/1937 | McConnell | 422/42 X |
| 2,390,843 | 12/1945 | McCauley et al. | 422/305 X |
| 2,440,082 | 4/1948 | Flanders et al. | 422/305 X |
| 2,497,612 | 2/1950 | Kutzman | 422/125 |
| 2,540,095 | 2/1951 | Buehler | 422/305 X |
| 2,590,529 | 3/1952 | Gillies et al. | 422/29 X |
| 2,682,461 | 6/1954 | Hutchison | 422/40 X |
| 2,690,501 | 9/1954 | Laibow | 422/305 X |
| 2,767,511 | 10/1956 | Kissner et al. | 422/306 X |
| 2,813,187 | 11/1957 | Rovira | 422/306 X |
| 3,446,893 | 5/1969 | Hanford et al. | 252/350 X |
| 3,645,931 | 2/1972 | Nornanton | 252/350 X |
| 3,748,438 | 7/1973 | Costello | 422/305 X |
| 3,806,323 | 4/1974 | Thompson | 422/126 X |
| 3,903,015 | 9/1975 | Roos et al. | 252/350 |
| 3,956,849 | 5/1976 | Radulesui | 424/42 X |
| 3,986,838 | 10/1976 | Reichert | 222/5 X |
| 4,163,038 | 7/1979 | Nishimura et al. | 422/36 |
| 4,171,340 | 10/1979 | Nishimura et al. | 422/36 |

FOREIGN PATENT DOCUMENTS

| | | |
|---|---|---|
| 46-19080 | 5/1971 | Japan . |
| 50-125309 | 10/1975 | Japan . |
| 673429 | 6/1952 | United Kingdom . |
| 699766 | 11/1953 | United Kingdom . |

Primary Examiner—Barry S. Richman
Attorney, Agent, or Firm—Armstrong, Nikaido, Marmelstein & Kubovcik

[57] ABSTRACT

A mixture of an active ingredient such as insecticide, fungicide, repellent or the like and a blowing agent is heated with a hot air current produced by a suitable heat source and a fan to thermally decompose the blowing agent and cause the hot air current and the gas resulting from the thermal decomposition to vaporize and diffuse the active ingredient. The mixture is accommodated within a passage formed in a container and the passage is provided therein with a fan for forcing the hot air current therethrough. A fumigating method and an apparatus of this invention ensure very efficient, quick and uniform diffusion of the vapor of the active ingredients and are usable for controlling vermin and other purposes with high safety and great convenience.

25 Claims, 6 Drawing Figures

FUMIGATING METHOD AND APPARATUS

This application is a continuation-in-part application of our copending application Ser. No. 882816 filed Mar. 2, 1978, now U.S. Pat. No. 4,171,340 issued Oct. 16, 1979.

This invention relates to a method of fumigating the interior of rooms and other confined spaces for controlling vermin, for repelling insects and rodents and for fungicidal and incensing purposes, and an apparatus therefor. More particularly this invention relates to fumigating method and apparatus which are capable of concentrically producing such effects within a short period of time e.g. a few minutes or ten-odd minutes. The present method and apparatus are especially useful for controlling noxious insects, such as mosquitoes, flies and cockroaches, which are detrimental to man and also other insects, such as plant lice, green house whiteflies and caterpillers, which are harmful to agricultural plants.

As a method of controlling noxious insects, fumigation is known in which compositions of an active chemical and a combustible material are used, such that the combustible material, when burned, gives off heat and smoke, the heat causing the active ingredient to concentrically vaporize within a short time and the smoke assisting the volatilization of the ingredient. In order to quickly volatilize a great amount of active ingredient, the combustible materials useful for fumigating compositions are those capable of evolving a large quantity of smoke. The large quantity of smoke emitted by such combustible material generally has a pungent odor and high toxicity, is harmful to the human body and might possibly be mistaken for a fire. Soot and the like contained in the smoke tend to soil household furniture and walls in rooms. The combustible material involves a fire hazard. Fumigators must therefore be handled with care. The known fumigators further have the serious drawback that the heat of combustion of the combustible material decomposes part of the active ingredient and results in a loss of the active ingredient, consequently affording a lower volatilization efficiency, namely lower effective fugacity rate and reduced efficacy. Measurements in the above method using various insecticides lead to effective fugacity rates lower than 10%. Thus the fumigators heretofore known are not usable with safety and convenience and are unsatisfactory in effectiveness.

An object of this invention is to provide a fumigating method which can be practiced with high safety substantially free of attendant smoke and without involving combustion and an apparatus therefor.

Another object of this invention is to provide a fumigating method and an apparatus therefor capable of effectively quickly giving off the vapor of an active ingredient without entailing a loss of the active ingredient due to the thermal decomposition thereof.

Still another object of this invention is to provide a fumigating method and an apparatus therefor capable of giving off the vapor of an active ingredient uniformly throughout a confined space within a short period of time to produce greatly improved insect-controlling effects.

These and other objects of this invention will become apparent from the following description.

This invention provides a fumigating method comprising heating a mixture of an active ingredient and a blowing agent with a hot air current to thermally decompose the blowing agent and cause the hot air current and the gas resulting from the thermal decomposition to vaporize and diffuse the active ingredient, the blowing agent being decomposable at a temperature of about 70° C. to about 300° C. to mainly evolve nitrogen gas.

Further this invention provides a fumigating apparatus for practicing the method of this invention comprising a container having a passage for forcing a hot air current therethrough, the passage being provided therein with a fan for forcing the hot air current and with a mixture of an active ingredient vaporizable and diffusable when heated with the hot air current and a blowing agent thermally decomposable when heated with the hot air current to promote the vaporization and diffusion of the active ingredient.

We have found that when the mixture of an active ingredient and a blowing agent is heated with a hot air current to thermally decompose the blowing agent and cause the resulting gas and the hot air current to vaporize the active ingredient, the active ingredient can be vaporized and dissipated very effectively substantially free of thermal decomposition. Stated more specifically, the hot air current when heating the mixture, initiates the blowing agent into thermal decomposition reaction first. Since this reaction is exothermic, the reaction once started in part of the blowing agent permits the heat of reaction to thermally decompose the whole blowing agent very rapidly in the mode of chain reaction, instantaneously giving off a large quantity of gas. The active ingredient is vaporized by being heated with the hot air current and the heat resulting from the thermal decomposition. The vapor of the active ingredient (and also an unvaporized portion of the ingredient as the case may be) is diffused through a confined space as entrained in the thermal decomposition gas. The hot air current serves to promote the diffusion of the ingredient. According to the invention, therefore, the gas produced by the decomposition of the blowing agent and the hot air current both act to diffuse a large quantity of the vapor of the active ingredient through the space in a substantially uniform, high concentration within a very short period of time, thus producing the desired insecticidal or like effects. Moreover, the method of this invention, in which the mixture of an active ingredient and a blowing agent is heated with a hot air current, can be practiced without using a combustible material which releases a toxic gas having a pungent odor when burned. The present method has another important feature that the active ingredient can be vaporized and diffused very effectively without any loss due to the thermal decomposition since it will in no way be exposed to a high temperature as of combusition heat but is heated moderately for an extremely short period of time.

The active ingredients useful in this invention are various and include those heretofore used for insecticidal, fungicidal repelling and incensing purposes. Typical of useful examples are as follows:

1. Insecticide (1) 3-allyl-2-methylcyclopenta-2-ene-4-one-1-yl dl-cis/-trans-chrysanthemate(available under the trademark "Pynamin", product of SUMITOMO CHEMICAL CO., LTD., Japan, hereinafter referred to as "allethrin A");

(2) 3-allyl-2-methylcyclopenta-2-ene-4-one-1-yl d-cis/-trans-chrysanthemate (available under the trademark "Pynamin-forte", product of SUMITOMO CHEMICAL CO., LTD., Japan, hereinafter referred to as "allethrin B");

(3) d-3-allyl-2-methylcyclopenta-2-ene-4-one-1-yl d-transchrysanthemate (available under the trademark "Exlin", product of SUMITOMO CHEMICAL CO., LTD., Japan);

(4) 3-allyl-2-methylcyclopenta-2-ene-4-one-1-yl d-trans-chrysanthemate;

(5) N-(3,4,5,6-tetrahydrophthalimide)-methyl dl-cis/-trans-chrysanthemate (available under the trademark "Neopynamin", product of SUMITOMO CHEMICAL CO., LTD., Japan, hereinafter referred to as "phthalthrin");

(6) 5-benzyl-3-furylmethyl d-cis/trans-chrysanthemate (available under the trademark "Chrysron-forte", product of SUMITOMO CHEMICAL CO., LTD., Japan, hereinafter referred to as "resmethrin");

(7) 5-propargyl-3-furylmethyl chrysanthemate;

(8) 3-phenoxybenzyl-2,2-dimethyl-3-(2',2'-dichloro) vinylcyclopropane-carboxylate (available under the trademark "Eksmin", product of SUMITOMO CHEMICAL CO., LTD., Japan, hereinafter referred to as "permethrin");

(9) 3-phenoxybenzyl d-cis/trans-chrysanthemate (available under the trademark "Sumithrin", product of SUMITOMO CHEMICAL CO., LTD., Japan, hereinafter referred to as "phenothrin");

(10) O,O-dimethyl O-(2,2-dichloro) vinylphosphate (hereinafter referred to as "DDVP");

(11) o-isopropoxyphenyl methylcarbamate;

(12) O,O-dimethyl O-(3-methyl-4-nitrophenyl)phosphorothioate;

(13) O,O-diethyl O-2-isopropyl-4-methyl-pyrimidyl-(6)-thiophosphate;

(14) O,O-dimethyl S-(1,2-dicarboethoxyethyl)-dithiophosphate;

(15) α-cyano-3-phenoxybenzyl 2-(4-chlorophenyl)-3-methylbutylate;

(16) α-cyano-3-phenoxybenzyl 2,2,3,3-tetramethylcyclopropanecarboxylate;

Among those insecticides, allethrin A, allethrin B, phthalthrin, resmethrin, permethrin, phenothrin and DDVP are most preferable.

2. Industrial fungicide (1) 2,4,4'-trichloro-2'-hydroxydiphenyl ether (hereinafter referred to as "IF-1");

(2) 2,3,5,6-tetrachloro-4-(methylsulfonyl)-pyridine (hereinafter referred to as "IF-2");

(3) alkylbenzyl dimethylammonium chloride (to be referred to as "IF-3");

(4) benzyldimethyl {2-[2-(p-1,1,3,3-tetramethyl-butylphenoxy)ethoxy]ethyl} ammonium chloride (to be referred to as "IF-4");

(5) N,N-dimethyl-N-phenyl-N'-(fluorodichloro methylthio) sulfonamide (hereinafter referred to as "IF-5");

(6) 2-(4'-thiazolyl)benzimidazole (hereinafter referred to as "IF-6");

(7) N-(fluorodichloromethylthio)-phthalimide (hereinafter referred to as "IF-7");

(8) 6-acetoxy-2,4-dimethyl-m-dioxine (hereinafter referred to as "IF-8");

(9) salicylic acid;
(10) formalin;
(11) 4-isopropyltropolone;
(12) p-chloro-m-xylenol;
(13) zinc bis (2-pyridinethiol-1-oxide);
(14) sodium-2-pyridinethiol-1-oxide;
(15) diiodo methyl-p-tolyl-sulfone;
(16) p-chlorophenyl-diiodomethyl sulfone;
(17) 2,4-hexadienoic acid;
(18) N-trichloromethylthio-4-cyclohexene-1,2-dicarboximide;
(19) 2,4,5,6-tetrachloro-isophthalonitrile;
(20) butyl-p-hydroxybenzoate;
(21) 3-trifluoromethyl-4,4'-dichlorocarbanilide;
(22) 2,2'-methylenebis[3,4,6-trichlorophenol];
(23) 2-hydroxyethyl-disulfide;
(24) β-phenoxyethylalcohol;
(25) 1,3-benzenediol;
(26) 1-dodecyl-2-methyl-3-benzyl-imidazolium chloride;
(27) alkyl-diaminoethylene glucine HCl;
(28) polymeric biguanide HCl;
(29) polyoctyl polyamino ethylglycine;
(30) hexahydro-1,3,5-tris-(2-hydroxyethyl)-S-triazine;
(31) polyhexamethylene biguanide HCl;
(32) poly [oxyethylene (dimethylimino) ethylene dichloride];
(33) alkylbetaine type S.A.A.;
(34) bis-(p-chlorophenyldiguanide)-hexanegluconate;
(35) S-bromo-S-nitro-1,3-dioxane;
(36) A mixture of 1,2-benzoisothiazoline-3-one, quarternary ammonium salt and propylene glycol;
(37) alkyldi-(aminoethyl)glycine;
(38) alkylisoquinolinium bromide;
(39) 3,4,4'-trichlorocarbanilide;
(40) decamethylene-bis-(4-aminoquinaldinium chloride);
(41) sodium dehydroxyacetate;
(42) 1-oxy-3-methyl-4-isopropylbenzene;
(43) 2-bromo-2-nitropropane-1,3-diol; (44) sodium p-toluenesulfon chloramide;
(45) 1-hexadecylpyridinium chloride;
(46) hexadecyltrimethylammonium bromide;

Among those industrial fungicides, IF-1 to IF-8 are preferable.

3. Antiseptic (1) α-bromo-cinnamaldehyde;
(2) N,N-dimethyl-N-phenyl-N'-(fluorodichloromethylthio)sulfamide;

4. Agricultural fungicide (1) A mixture of bis (dimethylthiocarbamoyl) disulfide, zinc dimethyldithiocarbamate and methylarsenic dimethyldithiocarbamate;
(2) S-benzyl diisopropyl phosphorothioate
(3) O-ethyl diphenyl phosphorodithioate;
(4) diethyl 4,4'-o-phenylenebis (3-thioallophanate);
(5) dimethyl 4,4'-o-phenylenebis (3-thioallophanate);
(6) N-(trichloromethylthio)-4-cyclohexene-1,2-dicarboximide;
(7) N-(1,1,2,2-tetrachloroethylthio)-4-cyclohexene-1,2-dicarboximide;
(8) S,S-6-methylquinoxaline-2,3-diyldithiocarbonate;
(9) pentachloronitrobenzene;
(10) methyl 1-(butylcarbamoyl)-2-benzimidazol carbamate;
(11) 2,4-dichloro-6-(o-chloroanilino)-1,3,5-triazine; (12) 2,3-dicyano-1,4-dithia-1,4-dihydroanthraquinone:
(13) 3-hydroxy-5-methylisoxazole;
(14) streptomycin;
(15) polyoxin:

(16) blasticidin S:
(17) kasugamycin:
(18) validamycin;
(19) 4,5,6,7-tetrachlorophthalide;
(20) N-(dichlorofluoromethylthio)-N',N'-dimethyl-N-phenylsulfamide:
(21) tetrachloroisophthalonitrile:
(22) 2,4-dichloro-6-(o-chloroanilino)-1,3,5-triazine:
(23) ethyl p,p'-dichlorobenzylate:
(24) zinc ethylenebis (dithiocarbamate);
(25) manganese ethylenebis(dithiocarbamate);
(26) complex of zinc and manganese ethylenebis(dithiocarbamate);
(27) dizinc bis(dimethyldithiocarbamate)ethylene bis(dithiocarbamate);
(28) bis(dimethyl-thiocarbamoyl)disulfide:
(29) isomeric reaction mixture of 2,6-dinitro-4-octylphenyl crotonate;

Among the above agricultural fungicides, those numbered (21)-(29) are preferable.

5. Insect-repellent (1) dimethyl phthalate;
(2) 2,3,4,5-bis-($\Delta_2$-butylene)-tetrahydrofuran;
(3) 2,3,4,5-bis-($\Delta_2$-butylene)-tetrahydrofurfuryl alcohol;
(4) N,N-diethyl-meta-toluamide;
(5) caprylicdiethylamide;
(6) 2,3,4,5-bis-($\Delta_2$-butylene)-tetrahydrofurfural;
(7) di-n-propyl isocinchomeronate;
(8) secondarybutyl styryl ketone;
(9) nonyl styryl ketone;
(10) N-propyl acetanilide;
(11) 2-ethyl-1,3-hexanediol;
(12) di-n-butyl succinate;
(13) 2-butoxyethyl-2-furfurylidene acetate;
(14) dibutyl phthalate;
(15) tetrahydrothiophene;
(16) β-naphthol;
(17) diallyl disulfide;
(18) bis-(dimethylthiocarbamoyl)disulfide;

6. Rodent-repellent (1) tetramethylthiuram disulfide;
(2) guanidine;
(3) naphthalene;
(4) cresol;
(5) cycloheximide;
(6) zincdimethyldithiocarbamate cyclohexylamine;
(7) N,N-dimethylsulfanildithiocarbamate;

7. Plant growth regulant (1) 4-chlorophenoxy acetic acid;
(2) gibberellin;
(3) N-(dimethylamino) succinamide;
(4) α-naphthylacetamide;

8. Herbicide (1) 2,4-D sodium salt;
(2) 3,4-dichloropropionanilide;

Among the above active ingredients, insecticides, fungicides and repellents are more suited for use in this invention. These active ingredients can be used conjointly with any of synergists, fugacity rate improving agents, deodorants, perfumes, etc. which are usually used. Preferable examples of the synergists are piperonyl butoxide, N-propyl isome, "MGK-264" (product of MCLAUGHLIN GORMLEY KING CO., U.S.A., "Cynepirin-222" (product of YOSHITOMI PHARMACEUTICAL INDUSTRIES LTD., Japan), "Cynepirin-500" (product of YOSHITOMI PHARMACEUTICAL INDUSTRIES LTD., Japan), "Lethane 384" (product of ROHM AND HAAS COMPANY, U.S.A.), "IBTA" (product of NIPPON FINE CHEMICAL CO., LTD., Japan), "S-421" (product of SANYO CHEMICAL INDUSTRIES, LTD., Japan). Preferable fugacity rate improving agents include phenethylisothiocyanate, dimethylester of himic acid, etc. Preferred deodorants are lauryl methacrylate (LMA), etc. Citral and citronellal are preferably usable as perfumes.

The blowing agent to be used conjointly with the active ingredient and, when desired, with various additives can be any of those generally used and capable of mainly evolving nitrogen gas on thermal decomposition. It is preferable to use organic compounds which will give off a gas at a temperature of between about 70° C. and about 300° C. The compounds having blowing temperatures far lower than 70° C. tend to decompose by themselves during storage. The compounds with blowing temperatures much higher than 300° C. are likely not to decompose when heated with hot air current. Accordingly such compounds are not preferable. Examples of typical organic blowing agents are listed in Table 1 below.

TABLE 1

| No. | Blowing agent | Abbreviation | Blowing temp. (°C.) |
|---|---|---|---|
| 1. | azodicarbonamide | AC | 200-210 |
| 2. | benzenesulfonylhydrazide | BSH | 100-160 |
| 3. | p-toluenesulfonylhydrazide | TSH | 110 |
| 4. | p,p'oxybis(benzenesulfonyl-hydrazide) | OSH | 140-160 |
| 5. | dinitrosopentamethylene-tetramine | DPT | 190-205 |
| 6. | N,N'dinitroso-N,N'-dimethylterephthalamide | DDTP | 90-105 |
| 7. | trihydrazinotriazine | THT | 235-290 |
| 8. | azobisisobutyronitrile | AIBN | 95-105 |
| 9. | 4,4'-azobiscyanovaleric acid | ACVA | 120 |
| 10. | t-butylazoformamide | BAFA | 147-149 |
| 11. | 2,4-bis-(azosulfonyl) toluene | 2,4-TSH | 108-109 |
| 12. | 2,2'azobisisobutyroamide | AZ-A | 92 |
| 13. | methyl-2,2'-azobisiso-butyrate | AZ-B | 85 |
| 14. | 2-(carbamoylazo)iso-butyronitrile | CIB | 105 |
| 15. | 1,1-azobiscyclohexane-1-carbonitrile | ACHC | 115 |

Among the blowing agents listed in Table 1, AC, OSH, AIBN and ACHC are preferable because they contribute to the increase in fugacity rate of an active ingredient. AC in particular remarkably enhances the fugacity rate thereof, produces a gas free of toxicity and pungent odor, and is therefore especially useful.

A blowing agent may be used with additives to reduce the blowing temperature. Preferable examples of the additives are as follows: "Dyhos" (product of NATIONAL LEAD CO., LTD., U.S.A.), "Tribase" (product of NATIONAL LEAD CO., LTD., U.S.A.), "OF-14" (product of ADECA ARGUS CO., LTD., U.S.A.), "OF-15" (product of ADECA ARGUS CO., LTD., U.S.A.), "KV-68A-1" (product of KYODO YAKUHIN CO., LTD., Japan), "Mark-553" (product of ARGUS CHEMI. CO., LTD., U.S.A.), "Sicostab 60" (product of G. Siegle & Co., U.S.A.), "Sicostab 61" (product of G. Siegle & Co., U.S.A.), Cd-stearate, Castearate, Zn-stearate, Zn-octate, ZnO, Sn-maleate, $ZnCO_3$, urea, chrome yellow, carbon black, etc.

According to this invention, the amount of the blowing agent relative to the active ingredient can be determined suitably depending on the use of the resulting composition. Usually it is preferable to use at least about one part by weight of the blowing agent per part by weight of the active ingredient. The effective fugacity rate progressively increases with increasing proportion of the blowing agent, but the use of too great an amount of the blowing agent will not produce significantly improved results. Preferably about one to about 20 parts by weight of the blowing agent is used per part by weight of the active ingredient. The active ingredient and the blowing agent are merely mixed together to prepare a fumigating mixture of this invention but, to ensure efficient production and ease of use, it is desirable to prepare the mixture in the form of powder, granules, pellets, otherwise shaped pieces, paste or the like or to enclose the mixture in a bag of meltable and incombustible resin. The mixture may also be enclosed in an openable bag made of aluminum or a bag of metal netting.

According to the invention, the mixture of an active ingredient and a blowing agent is heated with a hot air current which is produced by the use of a suitable heat source and a fan. Useful heat sources are not particularly limited, provided that the air heated therewith, when applied to the mixture by the fan, can give the mixture a temperature of about 70° C. to about 300° C. at which the blowing agent in the mixture is thermally decomposable. Examples of preferred heat sources are: (i) an exothermic substance capable of evolving heat by contact with water, (ii) an exothermic substance capable of evolving heat by contact with air, and (iii) means capable of evolving heat by application of an electric current.

Examples of typical exothermic substances to be used with water are calcium oxide, magnesium chloride, aluminum chloride, calcium chloride and ferric chloride, among which calcium oxide is most preferable since this compound gives off heat enough to elevate the temperature up to about 400° C. without producing any harmful substances due to hydrolysis thereof and the corrosion of a container accommodating this compound. For the most efficient heat generation, it is desirable that calcium oxide be in the form of about 1- to about 20-mesh pieces or grains. Preferably the reaction between calcium oxide and water is initiated not immediately after the addition of the latter to the former but after the water added thereto has uniformly and satisfactorily permeated into the calcium oxide.

To retard the initiation of the exothermic reaction when calcium oxide comes into contact with water, the pieces or grains of calcium oxide can be coated with at least one of mineral oils, vegetable oils and fats, higher alcohols, polyhydric alcohols, higher fatty acids and derivatives thereof. The amount of water to be used is preferably about 0.2 to about 3 times the stoichiometric amount, and is, for example, about 0.2 to about 3 moles per mole of calcium oxide. When blowing agents which will evolve a gas a lower temperatures are used, diatomaceous earth, acid clay, zeolite or like clay can be added to the exothermic substance so as to regulate the heating time and temperature to be given by the heat evolved from the substance.

Examples of exothermic substances using air are compounds which evolve heat on oxidation with the oxygen contained in air. More specific examples include a mixture of sodium sulfide and iron carbide and/or carbon black. Among them, a mixture of the above three substances is preferable. Preferably the mixture contains 40 to 60% by weight of sodium sulfide.

Examples of useful heat sources using an electric current are heating wires such as usual nichrome wires, heating carbon elements such as those produce by MATUSHITA ELECTRICAL INDUSTRIAL CO., LTD., Japan, semiconductors such as positive temperature coefficient thermistors, etc.

The air heated with the heat source is forced against the mixture of an active ingredient and a blowing agent by a fan to heat the mixture thereby decomposing the blowing agent to a gas and diffusing the active ingredient with the evolved gas. Examples of useful fans are those having blades which are rotatable, for example, by electric means such as dry cells, mechanical means such as spiral springs or rubber members and like means. The speed of rotation of the fan is usually about 600 to about 12,000 r.p.m. although suitably variable in accordance with the purpose of fumigation and the amount of the active ingredient. Preferably the blades are made of a material, such as iron, aluminum or like metal or heat-resistant plastics, having heat resistance capable of withstanding the hot air current to be produced.

The method of this invention can be practiced advantageously with use of an apparatus comprising a container having a passage for forcing a hot air current therethrough. The container is provided within the passage with the fan and the mixture of an active ingredient and a blowing agent. The container is made from a heat-resistant material such as an iron plate. To ensure safety in handling, the container preferably has an outer wall of heat insulating construction. The container and the passage formed therein for forcing a hot air current therethrough may be of any shape. Basically the container has an open upper portion and is formed in a lower portion of its side wall or a bottom wall with air inlets for drawing air into the container from outside as desired. The hollow interior of the container provides the passage. The passage is provided at an upper portion thereof with a partition adapted to place the mixture thereon and having air ports for passing the hot air current therethrough. Although the mixture can be placed on the partition in any form as in the form of a loose particles, it is desirable that the mixture be accommodated as contained, for example, in a meltable film bag. It is also preferable to place the mixture as contained in a bag of metal netting, which prevents the mixture from escaping through the air ports in the partition. The partition for placing the mixture thereon is replaceable by an inner case having suitable air ports in its bottom and fittable in the upper opening of the container. The inner case is convenient in that the mixture can be replaced as contained therein. The passage can be U-shaped to accommodate the mixture therein, with spaces formed in its bottom portion for passing the hot air current therethrough.

Preferably the fan is disposed between the air inlets formed in the container and the mixture accommodating portion within the passage, although positionable at any location insofar as the hot air current can be forced through the passage.

The heat source may be disposed outside the container or within the passage. Preferable heat sources which can be provided within the passage include, for example, an electric heating wire which generates heat when an electric current is passed therethrough. Usually the heating wire is interposed between the fan and the mixture accommodating portion, such that the air drawn into the container through the air inlets by the rotation of the fan is heated by the wire and applied to the mixture. The substance which evolves heat on contact with water or air is contained in a suitable receptacle and disposed outside the container, preferably as partitioned by a wall of the container which wall provides a heat transfer surface for heating the air to be drawn in through the air inlets. The receptacle for accommodating the exothermic substance may be optionally closed or opened, but is usually closed to eliminate heat losses. Preferably the receptacle has an outer wall of heat insulated construction to minimize the heat loss and assure safety in handling.

When using the exothermic substance capable of evolving heat by contact with water, the closed receptacle is provided with means for supplying water to the exothermic substance. For instance, the water supplying means is in the form of at least one water inlet aperture formed in lower portion of the closed receptacle or comprises a water reservoir which can be opened from outside.

The water reservoir is made from a film of easily breakable material such as an aluminum foil or synthetic resin film.

Examples of means for opening the water reservoir from outside, although not particularly limited, are preferably as follows:

(i) A thread attached to the water reservoir and adapted to be pulled from outside to break the portion of the reservoir where the thread is attached.
(ii) A needle adapted to puncture the water reservoir when pushed into the receptacle from outside.
(iii) A cutter provided within the receptacle and displaceable from outside to cut the water reservoir.
(iv) One of the means (i) to (iii) which is so arranged as to cause the exothermic substance to contact part of the water contained in the reservoir, permitting the resulting heat to melt and break the meltable film which forms the water reservoir. The sealing materials exemplified above are usable for the meltable film.

When the means (ii) or (iii) is used, the closed receptacle is provided with suitable means for restraining the needle or cutter from inadvertent displacement.

Preferably water can be applied to the exothermic substance in such a manner that water placed in the bottom of the receptacle is introduced through water inlet apertures in a lower part of the receptacle into a water-permeable layer provided in the closed receptacle from which the water comes into contact with the exothermic substance. The water-permeable layer, when employed, allows water to be applied to the exothermic substance uniformly over an increased area for efficient heat generation. The seeping rate of the water through the layer is suitably adjustable by varying the density, material and thickness of the layer. When such a water-permeable layer forms the bottom wall of the closed receptacle, water can be supplied to the exothermic substance without the ncessity of forming water inlet apertures in the bottom wall. Alternatively a water-permeable layer impregnated with water and sealed with a meltable film may be provided within the closed receptacle, preferably in combination with one of the opening means (i) to (iii) as already stated.

The water-permeable layer has numerous minute spaces as in open-cellular foamed materials and mats of fibrous material. The layer can be made from any water-permeable material. Examples of useful materials are woven and nonwoven fabrics of polyethylene, polypropylene, polyvinylidene chloride or like synthetic fibers, or of a blend of such synthetic fibers and cotton, mats of glass wool, asbestos, rock wool or like inorganic fibers, filter paper or like paper made of pulp, etc.

The exothermic substance capable of evolving heat by contact with air is usable in the form of particles to grains, a sheet or plate or in some other suitable form as contained in the receptacle of the apparatus. The exothermic substance must be held out of contact with air, namely in a hermetic state or in an inert gas atmosphere, before the use of the apparatus and must be maintained in contact with air during use. This can be done easily by enclosing the exothermic substance in a bag of material, such as an aluminum foil, which is impervious to air but readily openable, or by accommodating the exothermic substance in the open receptacle of the apparatus and sealing the opening as with aluminum film. In the latter case, it is preferable to place the exothermic substance into the receptacle in a nitrogen gas or like inert gas atmosphere. The exothermic substance thus enclosed can be exposed to air by opening the bag or the seal covering the opening of the receptacle.

The container or the inner case accommodating the mixture has an open upper end for volatilizing and diffusing the active ingredient, which may be kept sealed until the apparatus is put into use. When a material such as polyethylene, polypropylene, polyamide or the like which is meltable but is not burned with the application of hot air current, is used for sealing the open upper end of the apparatus, there is no need to remove the seal by hand when using the apparatus, nor any likelihood of hand coming into contact with the mixture, hence convenient and safe.

The meltable seal can be covered with another film or sheet for reinforcing the seal. The covering film or sheet has a number of perforations and may be made from metal such as iron, aluminum or alloy thereof, synthetic resin or paper.

The heat source, when energized or brought into contact with water or air, heats the air within the container. The hot air is forcibly brought into direct or indirect contact with the mixture by the fan within the passage, causing the thermal decomposition of the blowing agent and rapid vaporization of the active ingredient due to the heat of thermal decomposition of the blowing agent. The vapor of the active ingredient is rapidly and uniformly diffused through the atmosphere by the hot air current and the gas evolved from the thermal decomposition of the blowing agent. Especially according to this invention, the active ingredient can be very effectively volatilized in a large quantity and uniformly diffused throughout a confined space within a short period of time, e.g. a few minutes or ten-odd minutes, presumably because the blowing agent mixed with the active ingredient gives off a gas on decomposition, forcing the active ingredient to volatilize promptly from the interior of the mixture, the active agent per se remains free of decomposition due to combustion and the hot air current promotes the vigorous diffusion of the vaporized active ingredient.

The method of this invention, which is capable of very efficiently quickly uniformly releasing large quantities of vapors of active ingredients, is useful in controlling noxious insects, such as flies, mosquitoes, fleas, bed bugs, house ticks and cockroaches, which are detrimental to man, as well as plant lice, green house whiteflies, caterpillars and other insects which are harmful to agricultural plants, and is also serviceable for repelling above noxious insects or rodents, such as mice, rats and voles, and for fungicidal and incensing purposes. Additionally the present method is usable for these applications with high safety and great convenience substantially without involving combusition which would produce smoke with toxicity or a pungent odor.

This invention will be described below in greater detail with reference to apparatus suitable for practicing the present method and shown in the accompanying drawings, in which.

Figure 1:
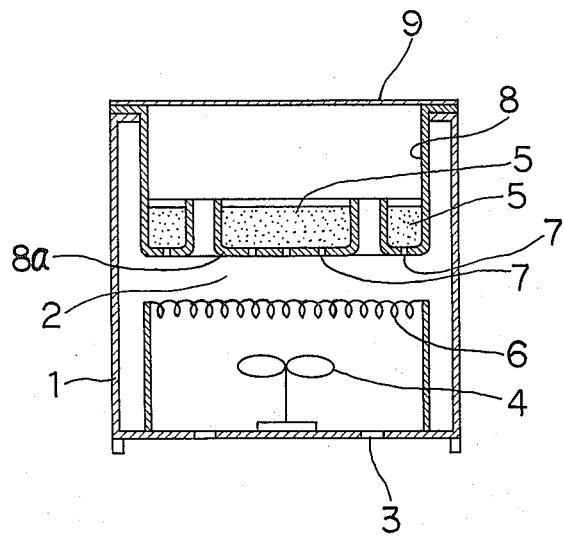
FIG. 1 is a view in vertical section showing a basic embodiment of the apparatus of the invention having a passage for forcing a hot air current therethrough and heating means for generating heat when energized.

FIGS. 1 to 6, in which like parts are referred to by like reference numerals, show a cylindrical container 1, a passage 2, air inlets 3, a fan 4, a mixture 5 of an active ingredient and a blowing agent and a heat source 6.

Figure 2:
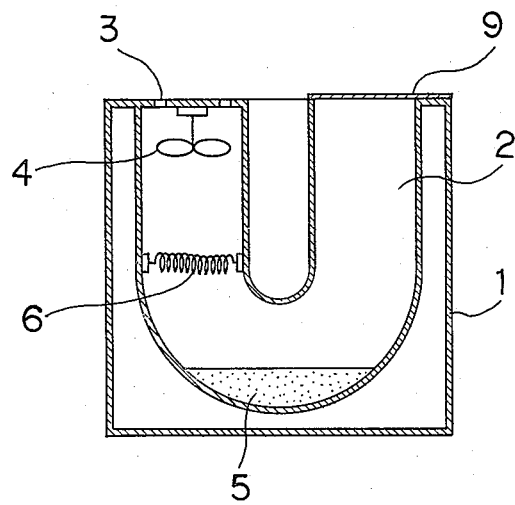
FIGS. 2 and 3 are views in vertical section showing modifications of the apparatus of FIG. 1.
Figure 3:
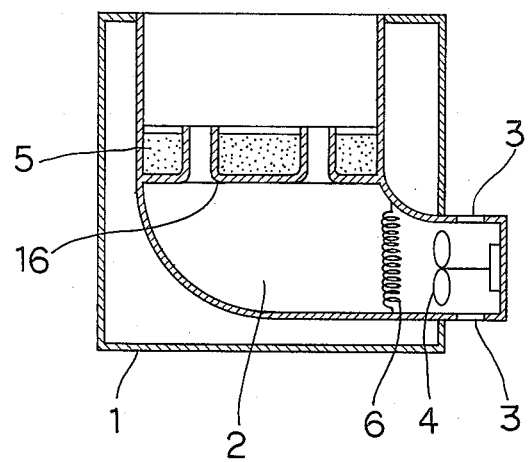

To use the embodiments of the invention shown in FIGS. 1 to 3, an electric current is passed through the heat source 6, and the rotatable blades of the fan 4 are driven, whereby the air drawn into the container 1 through the air inlets 3 is heated and forced through the passage 2 as a hot air current. The mixture 5 placed in the passage 2 in the form of powder is heated with the hot air current forced through the passage 2 directly as shown in FIG. 2 or indirectly through a partition i.e. a wall of mixture container 16 as seen in FIG. 3. This causes the thermal decomposition of the blowing agent contained in the mixture and the vaporization of the active ingredient therein, rapidly diffusing the resulting vapor of the ingredient through the atmosphere.

The mixture 5 in the form of shaped pieces may be disposed in the passage 2 on a removable inner case 8 having air ports 7 in its bottom as seen in FIG. 1. The mixture 5 can then be heated directly with the hot air entering the air ports 7 and indirectly through the wall of the inner case 8, especially through the bottom wall 8a thereof. The inner case 8 is safe and convenient to use since the mixture 5 can be replaced as contained in the case without touching the mixture with the hand.

The inner case 8 of the apparatus shown in FIG. 1 has its top opening sealed with a meltable film 9 which is spontaneously removable on melting when heated as with the hot air. The apparatus is therefore easy and convenient to use. Instead of sealing the top opening of the inner case 8 with the meltable film 9, a package of meltable film containing the mixture may be accommodated in the inner case 8, or the top surface of the mixture as contained in the inner case 8 may be covered directly with a meltable film in a sealing manner.

Figure 4:
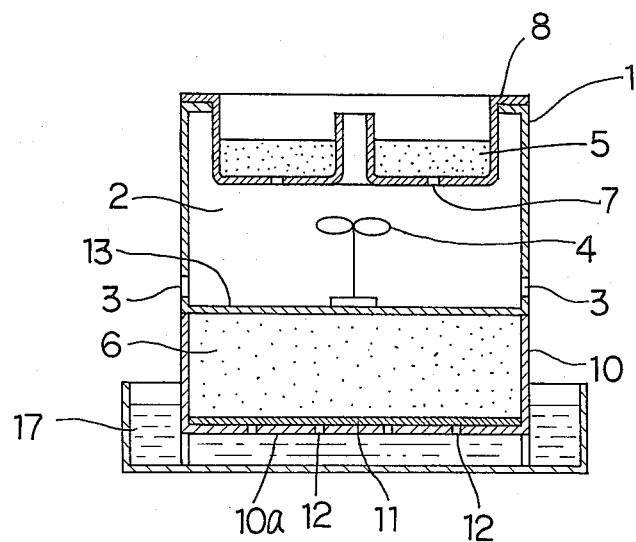
FIG. 4 is a view in vertical section showing another embodiment of the invention including as heating means a substance capable of evolving heat by contact with water.

The apparatus shown in FIG. 4 has a receptacle 10 attached to the bottom of the container 1 and containing a substance which evolves heat on contact with water. To use the apparatus, the bottom of the receptacle 10 is immersed in water 17, whereupon the water penetrates a water-permeable layer 11 through water inlets 12 formed in the bottom wall 10a of the receptacle 10, progressively seeping into the exothermic substance 6. The substance 6 thus brought into contact with the water evolves heat, with which the air drawn into the container 1 through the air intakes 3 is heated through a partition 13 i.e., the bottom wall of the container 1 providing a heat transfer surface. The fan 4 forces the hot air upward through the passage 2 as a hot air current. In the same manner as already described with reference to FIGS. 1 to 3, the hot air current therefore heats the mixture 5, causing the thermal decomposition of the blowing agent and vaporization of the active ingredient to vigorously diffuse the vapor of the ingredient.

With the apparatus shown in FIG. 4, the receptacle 10 for the exothermic substance is made removable for replacement, or the bottom wall 10a of the receptacle is rendered detachable so that the receptacle can be refilled with the exothermic substance. The water-permeable layer 11 illustrated in FIG. 4 causes water to uniformly seep into the receptacle 10 through the water inlets 12 to permit the substance to evolve heat very efficiently in contact with the water while completely preventing the exothermic substance from dropping through the water inlets 12 even when it is in the form of particles.

Figure 5:
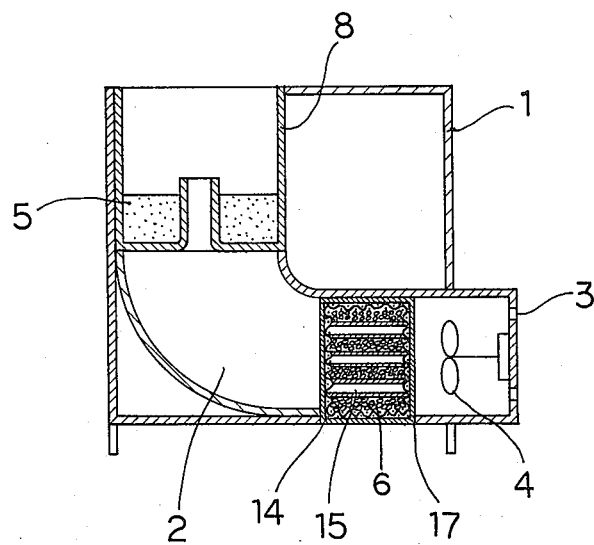
FIG. 5 is a view in vertical section showing another embodiment of the invention including as heating means a substance capable of evolving heat by contact with air.
Figure 6:
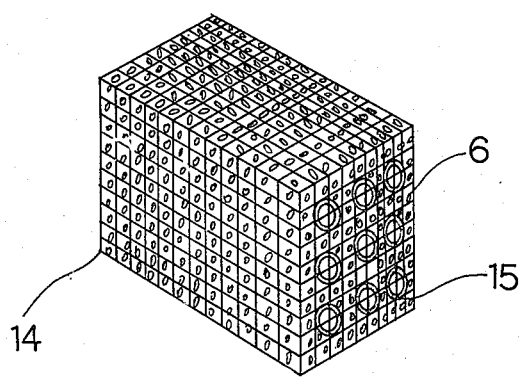
FIG. 6 is a perspective view showing a receptacle accommodating the substance capable of evolving heat by contact with air used in FIG. 5.

The apparatus in FIG. 5 has a receptacle of metal netting 14 detachably fitted in the passage 2 of the container 1. The receptacle 14 includes metal tubes 15 for the passage of air which are arranged therein as spaced apart from each other in a manner shown in FIG. 6 and accommodates, in the space formed among the tubes 15, an exothermic substance 6 which evolves heat on contact with air. To hold the exothermic substance 6 out of contact with air before the apparatus is put to use, the receptacle 14 is covered with an air-impermeable openable film 17 from outside of the metal netting.

When the apparatus is to be used, the film 17 is removed to expose the exothermic substance 6 to air for the evolution of heat. An electric current is applied to rotate the fan 4, whereby the air ingressing via air inlets 3 is forced into the metal tubes 15 and heated during the travel of the tubes by the heat evolved from the exothermic substance 6 by contact with air. The hot air current is then forced upward through the passage 2. In the same manner as described with reference to FIGS. 1 to 4, the hot air current heats the mixture 5 to vigorously vaporize the active ingredient and diffuse the vapor.

This invention will be described below in greater detail with reference to examples, in which the effective fugacity rates of active ingredients are determined by volatilizing the ingredient within a closed container, passing the air within the container through a solvent which completely dissolves the active ingredients, such as benzene, acetone, water, chloroform or dichloromethane to cause the solvent to absorb the vaporized ingredient in the air, concentrating the solvent and subjecting the concentrate to gas chromatography. The fugacity rate is expressed in terms of the ratio in percent of the quantity of the vaporized active ingredient to the quantity of the ingredient initially admixed with a blowing agent.

EXAMPLE 1

Each of the specimen mixtures of insecticide and blowing agent listed in Table 2 is placed in an inner case 8 (60 cm$^3$ in capacity) fitted in an apparatus (15 cm in diameter and 15 cm in height) provided in its passage 2 with the same ring heater 6 as shown in FIG. 1.

The ring heater 6 (power 400 W) and a fan 4 (with 4 blades) are energized to produce a hot air current. The fan 4 is driven at 3000 r.p.m. The mixture is heated for about 5 minutes (up to a temperature of about 300° C.) with the hot air current to thermally decompose the blowing agent and diffuse the vapor of the insecticide. The results are shown in Table 2.

TABLE 2

| Specimen No. | insecticide | (g) | blowing agent | (g) | effective fugacity rate (%) |
|---|---|---|---|---|---|
| 1. | allethrin B | 1 | AIBN | 5 | 79.1 |
| 2. | DDVP | 1 | TSH | 10 | 69.5 |
| 3. | " | 1 | 2,4-TSH | 10 | 72.1 |
| 4. | " | 1 | OSH | 10 | 78.6 |
| 5. | allethrin A | 1 | AZ-A | 10 | 66.5 |
| 6. | " | 1 | AZ-B | 10 | 65.1 |
| 7. | " | 1 | CIB | 10 | 70.9 |
| 8. | " | 1 | ACHC | 10 | 72.2 |
| 9. | resmethrin | 1 | AC | 5 | 80.3 |
| 10. | " | 1 | AC | 10 | 80.9 |
| 11. | phthalthrin | 1 | AC | 5 | 66.2 |
| 12. | phenothrin | 1 | AC | 5 | 75.1 |
| 13. | permethrin | 1 | AC | 5 | 72.9 |
| 14. | resmethrin | 1 | AC | 1 | 69.2 |
|  |  |  | AZ-B | 1 |  |
| 15. | allethrin B | 1 | AC | 1 | 71.5 |
|  |  |  | AIBN | 1 |  |

Table 2 shows that the method of this invention can achieve effective fugacity rates of more than 65%.

EXAMPLE 2

The same procedure as used in Example 1 is repeated with the exception that a blowing agent containing an additive is used. The results are also given in Table 3.

TABLE 3

| Specimen No. | insecticide | (g) | blowing agent | (g) | effective fugacity rate (%) |
|---|---|---|---|---|---|
| 16. | resmethrin | 1 | CELLMIC CAP* | 5 | 84.1 |
| 17. | " | 0.5 | CELLMIC AN** | 5 | 84.7 |

*"CELLMIC CAP" is an AC-type blowing agent manufactured by SANKYO KASEI CO., LTD.,Japan
**"CELLMIC AN" is a blowing agent manufactured by the same company and containing a mixture of 50% DPT and 50% urea as an additive.

Table 3 reveals that the use of the additive with the blowing agent achieves the results more excellent than those shown in Table 2.

EXAMPLE 3

The same procedure as used in Example 1 is repeated except that to the insecticide is added a synergist (for Specimens No. 18 to No. 22), a deodorant or perfume (for Specimens Nos. 23 and 24) or a fugacity rate improving agent (for Specimens Nos. 25 and 26) as shown in Table 4, which also shows the results.

TABLE 4

| Specimen No. | insecticide | (g) | additive | (g) | blowing agent | (g) | effective fugacity rate (%) |
|---|---|---|---|---|---|---|---|
| 18. | resmethrin | 1 | S-421 | 2 | AC | 3 | 76.5 |
| 19. | resmethrin | 1 | piperonyl butoxide | 3 | " | 5 | 81.1 |
| 20. | resmethrin | 1 | Lethane 384 | 3 | " | 5 | 82.3 |
| 21. | resmethrin | 1 | Cynepirine-222 | 3 | " | 5 | 84.2 |
| 22. | resmethrin | 1 | Cynepirine-500 | 3 | " | 5 | 83.0 |
| 23. | resmethrin | 0.5 | citral | 0.1 | " | 2 | 79.3 |
| 24. | resmethrin | 0.5 | LMA | 0.1 | " | 1 | 73.5 |
| 25. | resmethrin | 0.5 | phenethyl-isothiocyanate | 1 | CELLMIC AN | 5 | 86.9 |
| 26. | resmethrin | 0.5 | dimethyl ester of himic acid | 1 | CELLMIC AN | 5 | 86.3 |

Table 4 shows that the use of the additive with the active ingredient achieves the results as excellent as those shown in Table 2 and 3.

COMPARATIVE EXAMPLE 1

The same procedure as in Example 1 is repeated without using any blowing agent. Table 5 shows the results.

TABLE 5

| Specimen No. | insecticide | (g) | blowing agent | (g) | effective fugacity rate (%) |
|---|---|---|---|---|---|
| 27. | resmethrin | 1 | — | — | 0.4 |
| 28. | allethrin B | 1 | — | — | 0.6 |

COMPARATIVE EXAMPLE 2

Each of the mixtures listed in Table 6, composed of an insecticide and nitrocellulose known as a combustible material in conventional fumigants, is introduced into a cylindrical container 15 cm in diameter and 15 cm in height and burned for fumigation by the ignition with a match. The effective fugacity rates achieved are shown in Table 6.

TABLE 6

| Specimen No. | insecticide | (g) | combustable material | (g) | effective fugacity rate (%) |
|---|---|---|---|---|---|
| 29. | resmethrin | 0.5 | nitrocellulose (30%) | 30 | 6.3 |
| 30. | allethrin B | 0.5 | nitrocellulose (30%) | 30 | 1.6 |
| 31. | phthalthrin | 0.5 | nitrocellulose (30%) | 30 | 7.3 |
| 32. | phenothrin | 0.5 | nitrocellulose (30%) | 30 | 8.1 |
| 33. | permethrin | 0.5 | nitrocellulose (30%) | 30 | 8.5 |

Tables 2 to 6 show that the method of this invention using the present apparatus can achieve remarkably improved effective fugacity rate.

COMPARATIVE EXAMPLE 3

The mixtures listed in Table 7, each composed of an insecticide and a gas-generating chemical used in known fumigants, are introduced respectively into the same container as used in Comparative Example 2 and are ignited to vaporize the active ingredients. Table 7 shows the results.

TABLE 7

| Specimen No. | insecticide | (g) | Gas-generating chemical | (g) | effective fugacity rate (%) |
|---|---|---|---|---|---|
| 34. | resmethrin | 1.0 | ammonium nitrate | 6.0 | 9.4 |
| 35. | permethrin | 1.0 | ammonium nitrate | 6.0 | 8.9 |
| 36. | resmethrin | 1.0 | ammonium nitrate | 5.4 | 8.9 |
|  |  |  | potassium chromate | 0.6 |  |
| 37. | permethrin | 1.0 | ammonium nitrate | 5.4 | 8.6 |
|  |  |  | potassium chromate | 0.6 |  |
| 38. | resmethrin | 1.0 | guanidine nitrate | 6.0 | 10.8 |
| 39. | permethrin | 1.0 | guanidine nitrate | 6.0 | 10.5 |
| 40. | resmethrin | 1.0 | guanidine nitrate | 5.0 | 15.5 |
|  |  |  | tartaric acid | 1.0 |  |
| 41. | permethrin | 1.0 | guanidine nitrate | 5.0 | 14.6 |
|  |  |  | tartaric acid | 1.0 |  |

Table 7 shows that extremely low effective fugacity rates of only 15.5% or less can be obtained by these conventional fumigants.

Active ingredients placed in the present apparatus are tested for the quantity of smoke evolved, toxicity, insecticidal effect and concentration in air by being volatilized by the method of Example 1.

(I) Quantity of smoke (turbidity)

An apparatus of this invention accommodating the same mixture as Specimen No. 10 is used in a chamber 90 cm × 90 cm × 90 cm to volatilize the active ingredient (resmethrin). For comparison, a fumigating composition composed of 30 g of nitrocellulose (30%) and 1.5 g of DDVP is burned in the same chamber as above.

The chamber is transparent in the upper part and is lit up with a fluorescent light (20 w) provided in the upper center of the chamber. A marking plate is horizontally disposed in vertically movable manner in the chamber. The marking plate is a white disc made of plastic with a diameter of 35 mm. On the disc are drawn four black lines 0.5 mm in width such that two pairs of lines are intersected at a right angle in the center of the disc, two lines of each pair being spaced in parallel with a distance of 1.0 mm. The above disc is vertically moved to measure the longest distance (h) between the top of the chamber and the disc at which the four lines on the disc are clearly seen with unaided eyes. In this way, a turbidity within the chamber is calculated by the following equation.

$$\text{turbidity (\%)} = \frac{h \text{ (cm)}}{90 \text{ (cm)}} \times 100$$

The same procedure is repeated five times for each specimen, giving the following average data shown in Table 8.

TABLE 8

|  | distance (cm) | turbidity (%) |
|---|---|---|
| present invention: | 68 | 75.6 |
| Comparison: | 16 | 17.8 |

The results indicate that the quantity of smoke emitted from this invention is substantially negligible.

(II) Toxicity

A toxicity test is conducted under the following conditions.

(1) Apparatus
  A: Apparatus as used in Example 1 accommodating specimen No. 9 of this invention.
  B: Apparatus as used in Example 1 accommodating specimen No. 10 of this invention.
(2) Device
  Chambers, 1 m × 1 m × 1 m (i.e. 1 m³)
(3) Animals
  Five-week-old mice JCL: ICR
(4) Method
  Five male mice or five female mice are placed into a chamber. The interior of the chamber is fumigated with one or two apparatus and the animals are left confined in the chamber for 2 hours. The animals are thereafter placed into an ordinary cage and given a diet and water.
(5) Results
  Table 9 and 10 show the results.

TABLE 9

| | | number of deaths | | | | | |
|---|---|---|---|---|---|---|---|
| | | immediately after the fumigation | | one day after the fumigation | | two days after the fumigation | |
| Test No. | Apparatus | M. | F. | M. | F. | M. | F. |
| 1 | A (one) | 0 | 0 | 0 | 0 | 0 | 0 |
| 2 | B (one) | 0 | 0 | 0 | 0 | 0 | 0 |
| 3 | B (two) | 0 | 0 | 0 | 0 | 0 | 0 |

Specimens No. 9 and No. 10 used in the toxicity test produce no toxicity, and the test animals are alive 10 days after the fumigation. As shown in Table 9, high safety is ensured when using the present apparatus in a chamber having a conentration of the volatilized active ingredient over 30 times the concentration thereof at which a satisfactory insecticidal effect is achieved.

Table 10 shows the changes in the weight of the animals surviving the test.

TABLE 10

| | | changes in the average weight of the animals (g) | | | | | | |
|---|---|---|---|---|---|---|---|---|
| Test No. | animal's sex | before test | 1 day after | 2 days after | 4 days after | 6 days after | 8 days after | 10 days after |
| 1 | M. | 25.2 | 26.4 | 25.3 | 28.2 | 28.0 | 28.2 | 30.4 |
|  | F. | 24.2 | 24.5 | 23.9 | 25.0 | 24.5 | 24.0 | 25.5 |
| 2 | M. | 24.8 | 26.0 | 25.1 | 27.6 | 26.5 | 28.2 | 29.5 |
|  | F. | 25.5 | 25.6 | 24.9 | 27.0 | 26.5 | 27.1 | 27.5 |
| 3 | M. | 22.6 | 25.2 | 25.1 | 27.8 | 28.1 | 28.5 | 30.5 |
|  | F. | 22.1 | 22.4 | 22.0 | 23.0 | 23.9 | 24.0 | 25.1 |

Table 10 reveals that the specimens of the invention show substantially no harmful effect on the increasing rate of body weight of the tested animals and that they are substantially free from toxicity. The amounts of food taken by the animals is slightly reduced only on the first day after the test but thereafter no change is observed.

(III) Insecticidal effect

1. Apparatus of this invention are tested for insecticidal effect under the following conditions.
   (1) Test insects
      Adults of german cockroaches.
   (2) Method
      A laboratory dish (24 cm in inside diameter and 6.5 cm in height) containing 25 test insects is placed in each corner of a closed room, 3 m×4 m×3 m (height), i.e. 36 $m^3$, and the interior of the room is fumigated with apparatus as used in Example 1 containing the specimens No. 1, 10, 12 and 13 respectively placed in the center of the room. Knockdown is determined at a specified time interval after the initiation of fumigation. Two hours after the fumigation, the test insects are transferred to a rearing chamber, and mortality (%) is determined in 24 hours and 48 hours. In the rearing chamber, the insects are given a diet and water. Table 11 shows the results.

TABLE 11

| specimens No. | | 1 | 10 | 12 | 13 |
|---|---|---|---|---|---|
| | 30 min. | 60 | 55 | 55 | 50 |
| Knockdown | 60 min. | 100 | 100 | 100 | 90 |
| (%) | 90 min. | 100 | 100 | 100 | 100 |
| | 120 min. | 100 | 100 | 100 | 100 |
| Mortality | 24 hr. | 90 | 95 | 80 | 100 |
| (%) | 48 hr. | 100 | 100 | 100 | 100 |

Table 11 shows that the use of the present apparatus in a closed room leads to effective extermination of noxious vermin.

2. Apparatus of this invention are further tested for insecticidal effect in a simulated living room.
   (1) Test insects
      Adults of german cockroaches and adults of american cockroaches.
   (2) Method
      A 76-cm-high desk having four drawers in layers is placed in one corner of a closed room, 3 m in width, 4 m in length and 3 m in height, i.e. 36 $m^3$. A wood box (45 cm×41 cm×37 cm) is placed in another corner of the room as spaced apart by 2 cm from the wall, with its opening opposed to the wall. A closed box (measuring 30 cm×30 cm×30 cm and having 8 holes of 7 mm in diameter in its top side) is placed on a 150-cm-high shelf in the center of one of the longitudinal walls of the room, the box being positioned close to the wall.
      Laboratory dishes (24 cm in inside diameter and 6.5 cm in height) each containing 20 adults of german cockroaches and 10 adults of american cockroaches are placed in various locations within the room. The interior of the room is fumigated in the same manner as in Example 1 with a specimen placed in the center of the room, and the insects are left confined in the room for one hour. The insects are thereafter placed into a rearing case and given a diet and water. Mortality (%) is determined 24 hours and 48 hours after the start of the experiment.
      The dishes are placed in the following locations:
      $P_1$: In the open box.
      $P_2$: In the closed box.
      $P_3$: In the uppermost closed drawer of the desk.
      $P_4$: In the second highest drawer of the desk as withdrawn by 1 cm.
      $P_5$: In the lowermost drawer of the desk as withdrawn by 2 cm.
   (3) Specimens
      Specimen No. 10.
   (4) Results
      Table 12 shows the results achieved with the german cockroaches, and Table 13 those with american cockroaches.

TABLE 12

| | | Place | | | | |
|---|---|---|---|---|---|---|
| | | $P_1$ | $P_2$ | $P_3$ | $P_4$ | $P_5$ |
| Mortal- | 24 hr. | 60 | 45 | 60 | 50 | 45 |
| ity (%) | 48 hr. | 100 | 100 | 100 | 100 | 100 |

TABLE 13

| | | Place | | | | |
|---|---|---|---|---|---|---|
| | | $P_1$ | $P_2$ | $P_3$ | $P_4$ | $P_5$ |
| Mortal- | 24 hr. | 20 | 30 | 40 | 20 | 30 |
| ity (%) | 48 hr. | 100 | 70 | 100 | 90 | 100 |

Tables 12 and 13 show that the apparatus of this invention is very effective at various locations.

(IV) Concentration of active ingredient in air

An apparatus of this invention as shown in FIG. 1 and containing the mixture specimen No. 10 is placed on the floor in the center of a room (2.7 m×3.6 m×2.6 m, i.e. 25.3 $m^3$), and the active ingredient is vaporized in the same manner as in Example 1.

With the commencement of fumigation, the interior air is passed at a rate of 1.0 liter/min through benzene placed in each of three collectors which are arranged at the following three locations within the room, $A_1$ to $A_3$, respectively, and the active component in the air is completely dissolved in the benzene for collection.
$A_1$: 2.25 m away from the apparatus, 1 m above the floor at a corner of the room.
$A_2$: 1 m immediately above the apparatus.
$A_3$: 1.35 m away from the apparatus; 1 m above the floor at the center of a side wall of the room.

Over the period of 6 hours and 15 minutes following the start of the fumigation, the benzene in each collector is replaced every 15 minutes, i.e. 25 times, and each benzene portion is conentrated. Triphenyl phosphate (TPP) serving as an internal standard substance is added to the concentrate, and the mixture is further concentrated to about 1 ml to prepare a specimen solution. The quantity of the active ingredient in the specimen solution is determined by gas chromatography, and the concentration of the active ingredient in 1 $m^3$ of the air (mg/$m^3$) is determined during fumigation at an interval of every 15 minutes. Table 14 shows the results.

TABLE 14

| Time | Locations | | |
|---|---|---|---|
| (min.) | $A_1$ | $A_2$ | $A_3$ |
| 0-15 | 21.41 | 21.60 | 21.85 |
| 30-45 | 18.05 | 18.14 | 18.90 |
| 60-75 | 14.86 | 14.95 | 15.07 |
| 120-135 | 9.35 | 9.40 | 9.83 |
| 180-195 | 4.21 | 4.25 | 4.40 |
| 240-255 | 1.15 | 1.18 | 1.21 |
| 300-315 | 0.30 | 0.34 | 0.36 |

TABLE 14-continued

| Time | Locations | | |
|---|---|---|---|
| (min.) | $A_1$ | $A_2$ | $A_3$ |
| 360–375 | 0.04 | 0.04 | 0.05 |

Table 14 shows that the present apparatus achieves uniform diffusion of the active ingredient at locations $A_1$ to $A_3$ in the rooom.

EXAMPLE 4

A mixture of an insecticide and a blowing agent as listed in Table 15 is placed into an apparatus of this invention utilizing 100 g of calcium oxide (1- to 5-mesh pieces) and shown in FIG. 4. The apparatus is brought to contact with water and 40 g of water enters into a receptacle 10 accommodating calcium oxide 6 via inlet apertures 12 in its bottom wall 10a to heat the air and the heated air is sent towards the mixture 5 by a fan 4 driven at 3000 r.p.m. The mixture is heated to a temperature of up to about 300° to about 350° C. with the hot air current, whereby the blowing agent is thermally decomposed to volatilize the insecticide. The effective fugacity rate of the insecticide is determined.

The results are shown in Table 15.

TABLE 15

| Specimen No. | insecticide | (g) | blowing agent | (g) | effective fugacity rate (%) |
|---|---|---|---|---|---|
| 42. | allethrin B | 1 | AC | 5 | 91.0 |
| 43. | resmethrin | 1 | BSH | 1 | 65.1 |
| 44. | " | 1 | AC | 3 | 77.8 |
| 45. | " | 1 | AC | 5 | 87.6 |
| 46. | " | 0.5 | AC | 2 | 78.7 |
| 47. | " | 0.5 | AC | 4 | 88.2 |
| 48. | " | 0.5 | AC | 5 | 86.4 |
| 49. | " | 0.5 | AC | 10 | 83.8 |
| 50. | phthalthrin | 1 | DDTP | 5 | 63.2 |
| 51. | phenothrin | 0.5 | THT | 5 | 72.7 |
| 52. | " | 1 | ACVA | 5 | 75.1 |
| 53. | permethrin | 0.5 | BAFA | 5 | 75.0 |
| 54. | " | 1 | AC | 5 | 83.0 |
| 55. | DDVP | 0.5 | AC | 5 | 83.3 |

Table 15 shows that the process of this invention results in remarkably improved effective fugacity rate.

The specimen No. 48 is tested for the quantity of smoke evolved (turbidity), toxicity and insecticidal effect described above. The results of the above tests are substantially the same as those of the tests using the specimen No. 10.

COMPARATIVE EXAMPLE 4

The same procedure as in Example 4 is repeated without using any blowing agent. Table 16 shows the results.

TABLE 16

| Specimen No. | insecticide | (g) | effective fugacity rate (%) |
|---|---|---|---|
| 56. | resmethrin | 1 | 0.5 |
| 57. | allethrin B | 1 | 2.7 |
| 58. | phenothrin | 1 | 1.4 |
| 59. | permethrin | 1 | 0.8 |

Tables 15 and 16 show that the method of this invention using the present apparatus results in remarkably improved effective fugacity rate.

EXAMPLE 5

A mixture of an insecticide and a blowing agent as listed in Table 17 is placed into the inner case 8 of the apparatus of this invention as shown in FIG. 5. A heating source (20 g) in the form of a mixture of 4 parts by weight of sodium sulfide and 6 parts by weight of iron carbide is brought into contact with air by opening the film 17 to heat the air entering the metal tubes 15 via air inlets 3 by the fan 4 driven at 3000 r.p.m. to about 300° C., whereby the mixture 5 placed in the passage 2 is heated with the hot air current travelling the passage 2 via the metal tubes 15 and the blowing agent is thermally decomposed to volatilize the insecticide. The effective fugacity rate achieved by the insecticide is determined. Table 17 shows the results.

TABLE 17

| Specimen No. | insecticide | (g) | blowing agent | (g) | effective fugacity rate (%) |
|---|---|---|---|---|---|
| 60. | allethrin B | 1 | AIBN | 5 | 72.8 |
| 61. | DDVP | 1 | TSH | 10 | 63.5 |
| 62. | DDVP | 1 | 2,4-TSH | 10 | 64.8 |
| 63. | allethrin B | 1 | AC | 3 | 77.0 |
| 64. | allethrin A | 1 | AZ-A | 10 | 66.4 |
| 65. | " | 1 | AZ-B | 10 | 64.2 |
| 66. | allethrin B | 1 | AC | 5 | 84.0 |
| 67. | allethrin A | 1 | ACHC | 10 | 68.5 |
| 68. | resmethrin | 1 | AZ-B | 10 | 63.5 |
| 69. | " | 1 | AC | 3 | 73.7 |
| 70. | " | 1 | AC | 5 | 79.6 |
| 71. | " | 0.5 | DPT | 1.5 | 82.1 |
| 72. | phthalthrin | 0.5 | AZ-A | 10 | 63.2 |

Table 17 shows that the method of this invention using the present apparatus results in remarkably improved effective fugacity rate.

EXAMPLE 6

The procedure of Example 1 is repeated using the same apparatus as used therein, the apparatus containing a mixture of fungicide and blowing agent listed in Table 18, which also shows the results.

TABLE 18

| Specimen No. | fungicide | (g) | blowing agent | (g) | effective fugacity rate (%) |
|---|---|---|---|---|---|
| 73. | IF-2 | 0.5 | AIBN | 5 | 64.5 |
| 74. | " | 0.5 | AC | 5 | 74.9 |
| 75. | " | 0.5 | AZ-A | 10 | 63.7 |
| 76. | IF-8 | 0.5 | AZ-B | 10 | 64.3 |
| 77. | " | 0.5 | AIBN | 5 | 60.7 |
| 78. | " | 0.5 | ACHC | 5 | 65.4 |
| 79. | IF-7 | 0.5 | AZ-B | 5 | 64.1 |
| 80. | " | 0.5 | AC | 5 | 68.2 |
| 81. | " | 0.5 | CIB | 5 | 61.2 |
| 82. | IF-6 | 0.5 | DPT | 1.5 | 75.7 |
| 83. | IF-3 | 0.5 | AZ-A | 3 | 85.6 |
| 84. | IF-2 | 0.5 | AIBN | 10 | 74.8 |
| 85. | IF-1 | 0.5 | AIBN | 5 | 79.0 |
| 86. | IF-4 | 0.5 | AIBN | 5 | 60.1 |
| 87. | IF-7 | 1 | AZ-A / AZ-B | 2 / 2 | 60.8 |

COMPARATIVE EXAMPLE 5

The procedure of Example 6 is repeated using an fungicide listed in Table 19 but without using any blowing agent. Table 19 also shows the results.

TABLE 19

| Specimen No. | fungicide | (g) | effective fungacity rate (%) |
|---|---|---|---|
| 88. | IF-5 | 1 | 6.9 |
| 89. | IF-8 | 1 | 8.8 |
| 90. | IF-7 | 1 | 2.0 |
| 91. | IF-2 | 1 | 10.1 |

Tables 18 and 19 reveal that the use of blowing agent conjointly with fungicide enables the fungicide to volatilize with an efficiency which is extremely high as compared with the efficiency achieved by the same quantity of the fungicide at the same temperature.

EXAMPLE 7

The procedure of Example 4 is repeated using a fungicide listed in Table 20 in place of the insecticide. Table 20 also shows the results.

TABLE 20

| Specimen No. | fungicide | (g) | blowing agent | (g) | effective fungacity rate (%) |
|---|---|---|---|---|---|
| 92. | IF-2 | 0.5 | AIBN | 5 | 63.1 |
| 93. | " | 0.5 | AC | 5 | 74.8 |
| 94. | " | 0.5 | AZ-A | 10 | 70.0 |
| 95. | IF-8 | 0.5 | AZ-B | 10 | 70.1 |
| 96. | " | 0.5 | AIBN | 5 | 71.8 |
| 97. | " | 0.5 | ACHC | 5 | 60.7 |
| 98. | IF-7 | 0.5 | AZ-B | 5 | 60.8 |
| 99. | " | 0.5 | AC | 5 | 75.3 |
| 100. | IF-6 | 0.5 | DPT | 1.5 | 70.1 |
| 101. | IF-3 | 0.5 | AZ-A | 3 | 92.3 |
| 102. | IF-2 | 0.5 | AIBN | 10 | 74.9 |
| 103. | IF-1 | 0.5 | AIBN | 5 | 75.1 |

COMPARATIVE EXAMPLE 6

The procedure of Example 7 is repeated using an fungicide listed in Table 21 but without using any blowing agent. Table 21 also shows the results.

TABLE 21

| Specimen No. | fungicide | (g) | effective fungacity rate (%) |
|---|---|---|---|
| 104. | IF-5 | 1 | 6.5 |
| 105. | IF-8 | 1 | 8.7 |
| 106. | IF-7 | 1 | 16.0 |
| 107. | IF-2 | 1 | 10.5 |

Tables 20 and 21 show that the present invention results in remarkably improved effective fugacity rate.

We claim:

1. A fumigating method comprising heating a mixture of an active ingredient and a blowing agent with a hot air current to thermally decompose the blowing agent without entailing combustion and cause the hot air current and the gas resulting from the thermal decomposition to vaporize and diffuse the active ingredient, the blowing agent being decomposable at a temperature of about 70° C. to about 300° C. to mainly evolve nitrogen gas and contacting an object, material or an area to be treated with the so-generated fumigant.

2. A fumigating method as defined in claim 1 wherein the active ingredient is an insecticide.

3. A fumigating method as defined in claim 1 wherein the active ingredient is a fungicide.

4. A fumigating method as defined in claim 1 wherein the hot air current has a temperature of about 70° C. to about 300° C.

5. A fumigating method as defined in claim 1 wherein the air current is produced by a fan.

6. A fumigating method as defined in claim 5 wherein the fan is driven at about 600 to about 12000 r.p.m.

7. A fumigating method as defined in claim 1 wherein the blowing agent is at least one species selected from the group consisting of azodicarbonamide, benzenesulfonylhydrazide, p-toluenesulfonylhydrazide, p,p'-oxybis(benzenesulfonylhydrazide), dinitrosopentamethylenetetramine, N,N'-dinitroso-N,N'-dimethylterephthalamide, trihydrazinotriazine, azobisisobutyronitrile, 4,4'-azobiscyanovaleric acid, t-butylazoformamide, 2,4-bis-(azosulfonyl)toluene, 2,2'-azobisisobutyloamide, methyl-2,2'-azobisisobutyrate, 2-(carbamoylazo)isobutyronitrile and 1,1'-azobiscyclohexane-1-carbonitrile.

8. A fumigating method as defined in claim 7 wherein the blowing agent is at least one species selected from the group consisting of azodicarbonamide, p,p'-oxybis(benzenesulfonylhydrazide), azobisisobutyronitrile and 1,1'-azobiscyclohexane-1-carbonitrile.

9. A fumigating method as defined in claim 8 wherein the blowing agent is azodicarbonamide.

10. A fumigating apparatus comprising a container having a passage for forcing a hot air current therethrough, the passage being provided therein with a fan for forcing the hot air current and with a mixture of an active ingredient vaporizable and diffusable when heated with the hot air current and a blowing agent thermally decomposable when heated with the hot air current to promote the vaporization and diffusion of the active ingredient, said blowing agent being decomposable at a temperature of about 70° C. to about 300° C. to give off mainly nitrogen gas.

11. A fumigating apparatus as defined in claim 10 wherein the mixture is contained in a replaceable bag of netting.

12. A fumigating apparatus as defined in claim 10 wherein the mixture is contained in a replaceable case having air ports.

13. A fumigating apparatus as defined in claim 10 wherein the fan is driven at about 600 to about 12000 r.p.m.

14. A fumigating apparatus as defined in claim 10 wherein the active ingredient is an insecticide.

15. A fumigating apparatus as defined in claim 10 wherein the active ingredient is a fungicide.

16. A fumigating apparatus as defined in claim 10 wherein the passage has an open upper end sealed with a meltable film.

17. A fumigating apparatus as defined in claim 16 wherein the meltable film is reinforced with a reinforcing film.

18. A fumigating apparatus as defined in claim 10 wherein the blowing agent is at least one species selected from the group consisting of azodicarbonamide, benzenesulfonylhydrazide, p-toluenesulfonylhydrazide, p,p'-oxybis(benzenesulfonylhydrazide), dinitrosopentamethylenetetramine, N,N'-dinitroso-N,N'-dimethyl-terephthalamide, trihydrazinotriazine, azobisisobutyronitrile, 4,4'-azobiscyanovaleric acid, t-butylazoformamide, 2,4bis-(azosulfonyl)toluene, 2,2'-azobisisobutyloamide, methyl-2,2'-azobisisobutyrate, 2-(carbamoylazo)isobutyronitrile and 1,1'-azobiscyclohexane-1-carbonitrile.

19. A fumigating apparatus as defined in claim 18 wherein the blowing agent is at least one species selected from the group consisting of azodicarbonamide, p,p'-oxybis(benzenesulfonylhydrazide), azobisisobutyronitrile and 1,1'-azobiscyclohexane-1-carbonitrile.

20. A fumigating apparatus as defined in claim 10 wherein means is provided for heating the air within the passage to produce the hot air current.

21. A fumigating apparatus as defined in claim 20 wherein the heating means is a means capable of evolving heat by application of an electric current.

22. A fumigating apparatus as defined in claim 20 wherein the heating means is an exothermic substance capable of evolving heat by contact with air.

23. A fumigating apparatus as defined in claim 20 wherein the heating means is an exothermic substance capable of evolving heat by contact with water.

24. A fumigating apparatus as defined in claim 23 wherein the substance is accommodated in a closed receptacle which is provided with means for supplying water to the substance.

25. A fumigating apparatus as defined in claim 24 wherein the closed receptacle is provided therein with a water-permeable layer through which the water from the water supplying means comes into contact with the substance.

* * * * *